(12) United States Patent
Conrad et al.

(10) Patent No.: US 11,540,844 B2
(45) Date of Patent: Jan. 3, 2023

(54) DISPOSABLE ACETABULAR MODULAR REAMER AND METHODS

(71) Applicant: Zimmer, Inc., Warsaw, IN (US)

(72) Inventors: Steven Conrad, Albion, IN (US); Thomas Cassidy, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 133 days.

(21) Appl. No.: 16/698,364

(22) Filed: Nov. 27, 2019

(65) Prior Publication Data

US 2020/0170653 A1 Jun. 4, 2020

Related U.S. Application Data

(60) Provisional application No. 62/772,736, filed on Nov. 29, 2018.

(51) Int. Cl.
*A61B 17/00* (2006.01)
*A61B 17/16* (2006.01)
*A61F 2/46* (2006.01)

(52) U.S. Cl.
CPC ........ *A61B 17/1642* (2013.01); *A61F 2/4603* (2013.01); *A61F 2/4609* (2013.01); *A61F 2/4612* (2013.01); *A61B 17/00234* (2013.01); *A61B 17/1666* (2013.01); *A61B 17/1684* (2013.01); *A61B 2017/0023* (2013.01); *A61B 2017/00526* (2013.01); *A61B 2017/1602* (2013.01)

(58) Field of Classification Search
CPC combination set(s) only.
See application file for complete search history.

(56) References Cited

U.S. PATENT DOCUMENTS

| 2011/0202060 A1* | 8/2011 | White | A61B 17/1666 |
| | | | 606/80 |
| 2016/0089158 A1 | 3/2016 | Fortin et al. | |
| 2019/0083110 A1* | 3/2019 | Wozencroft | A61B 17/8863 |

FOREIGN PATENT DOCUMENTS

| EP | 2359755 | 8/2011 |
| EP | 3127494 | 2/2017 |
| WO | WO-2020113072 A1 | 6/2020 |

OTHER PUBLICATIONS

"International Application Serial No. PCT US2019 063703, International Search Report dated Feb. 25, 2020", 4 pages.

(Continued)

*Primary Examiner* — Sameh R Boles
(74) *Attorney, Agent, or Firm* — Schwegman Lundberg & Woessner, P.A.

(57) ABSTRACT

Described herein are examples of orthopedic reamer heads for preparing a bone to receive an implant, as well as methods of assembling reamer heads. An illustrative example of a modular reamer head can include a body and a cutting system. The body can include a generally dome shape having an outer surface extending from an apex region to a base. The outer surface can have a recess including one or more arcuate channels that extend from the apex region towards the base of the dome. The cutting system can have one or more arcuate elements having cutting elements. One or more arcuate elements can extend from first end portions in the apex region towards second end portions proximate the base. At least a portion of the one or more arcuate elements can be located in the one or more arcuate channels to extend outward beyond the outer surface.

14 Claims, 9 Drawing Sheets

(56) References Cited

OTHER PUBLICATIONS

"International Application Serial No. PCT US2019 063703, Written Opinion dated Feb. 25, 2020", 6 pages.
"International Application Serial No. PCT/US2019/063703, International Preliminary Report on Patentability dated Jun. 10, 2021", 8 pgs.
"European Application Serial No. 19824127.5, Response to Communication pursuant to Rules 161(1) and 162 EPC filed Jan. 19, 2022", 15 pages.

* cited by examiner

DISPOSABLE ACETABULAR MODULAR REAMER AND METHODS

CLAIM OF PRIORITY

This application claims the benefit of U.S. Provisional Patent Application Ser. No. 62/772,736, filed on Nov. 29, 2018, the benefit of priority of which is claimed hereby, and which is incorporated by reference herein in its entirety.

TECHNICAL FIELD

This document pertains generally, but not by way of limitation, to orthopedic devices, and, more particularly, to reamer heads and methods of manufacturing reamer heads.

BACKGROUND

Bone degradation, disease and injury are a common occurrence that can be treated with surgical intervention using an orthopedic device such as an orthopedic implant. Orthopedic implants can be used, for example, to replace a joint or portion of a joint, or to provide fixation to a fractured bone while it heals.

In order to implant an orthopedic device, such as a hip implant, the surgeon can prepare the bone surface by a process such as reaming. Reaming can be accomplished using a reamer head having cutting elements thereon. The reamer head can be rotated to remove and shape the bone at the implant site. One such implant site can include an acetabulum of a hip bone, and the bone can be shaped to mimic the natural hemispherical shape of an acetabulum.

To provide rotation for the reaming process, the reamer head can include a driver interface that can be attached to a universal driver. When the reamer head is rotated by the universal driver with the reamer head located at a bone surface, the cutting elements on the reamer head remove the bone material.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

DETAILED DESCRIPTION

Figure 1A:
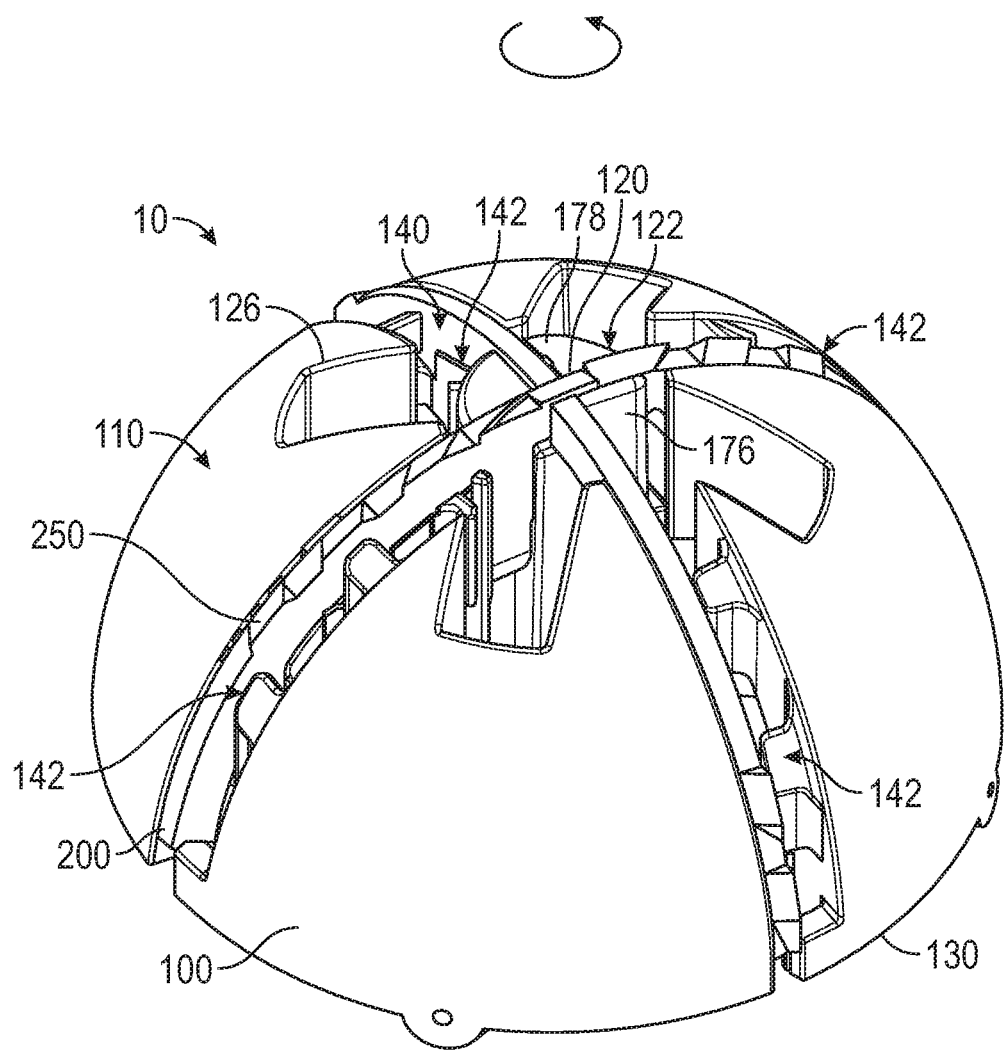
FIG. 1A shows a perspective view of an illustrative orthopedic reamer head including a body and a cutting system, in accordance with at least one example.

As discussed above, orthopedic implants can be secured to bone to replace a joint or a portion of a joint. To implant an orthopedic device, the surgeon can prepare the bone by removing bone material and shaping the bone to receive the implant.

In some hip replacement procedures, to remove and shape the bone, the surgeon can ream the bone surface using a driver that is adapted to interface with a reamer head. The reamer head can include cutting elements, that, when rotated by the driver, scrape the bone surface to remove bone and carry the bone away from the implant site.

Conventional reamer heads are generally cleaned and sterilized after a surgery and reused between patients. Cleaning and sterilizing can be expensive and not all hospitals are able to staff the cleaning facilities all the time. In addition, even after cleaning and sterilizing, the possibility of cross-contamination between patients can still occur.

The reamer heads and methods of manufacturing described herein reduce the cost to produce the reamer head. Therefore, it can be feasible to provide the reamer head as a disposable, one-time use product. A disposable reamer head eliminates the need to clean and sterilize the reamer head and eliminates a source of cross-contamination between patients.

FIGS. 1A, 1B and 2-6 show various views of an illustrative example of an orthopedic reamer head 10 and elements thereof. As a general overview and as shown in the perspective view of the reamer head 10, the orthopedic reamer head 10 can include a body 100 and a cutting system 200. Together the body 100 and the cutting system 200 form a reamer head 10 having a modular design.

The shape of the body 100, when rotated, can facilitate reaming an acetabulum to prepare the acetabulum to receive an implant. When the body 100 is rotated, the reamer head 10 is configured to ream a generally hemispherical shape to approximate the shape of an acetabulum or acetabular implant.

In some examples, the body 100 can be generally dome-shaped and/or generally hemispherical-shaped. In some examples, a generally hemispherical-shaped dome is not necessarily a perfect or complete hemisphere, but rather the body 100 has a generally hemispherical form or is provided as a portion of a dome or a portion of a hemisphere. A hemispherical shape can include a generally or substantially hemispherical shape configured to prepare the bone for an acetabular implant, or an implant at another ball and socket joint such as a shoulder joint.

To prepare the bone surface, the reamer head 10 is rotated at a bone surface using rotational motion provided by a driver (e.g., a universal driver). The body 100 of the reamer head 10 can include a driver interface 170 (FIGS. 3, 5 and 6) that is configured to be coupled to a driver to receive the rotational motion from the driver. The driver interface 170 can be cross-shaped and can extend across the base 130 of the body 100.

In some examples, the body 100, including the driver interface 170 can be integrally molded as one-piece component including a common polymeric material for the entire body 100 including the driver interface 170.

Figure 3:
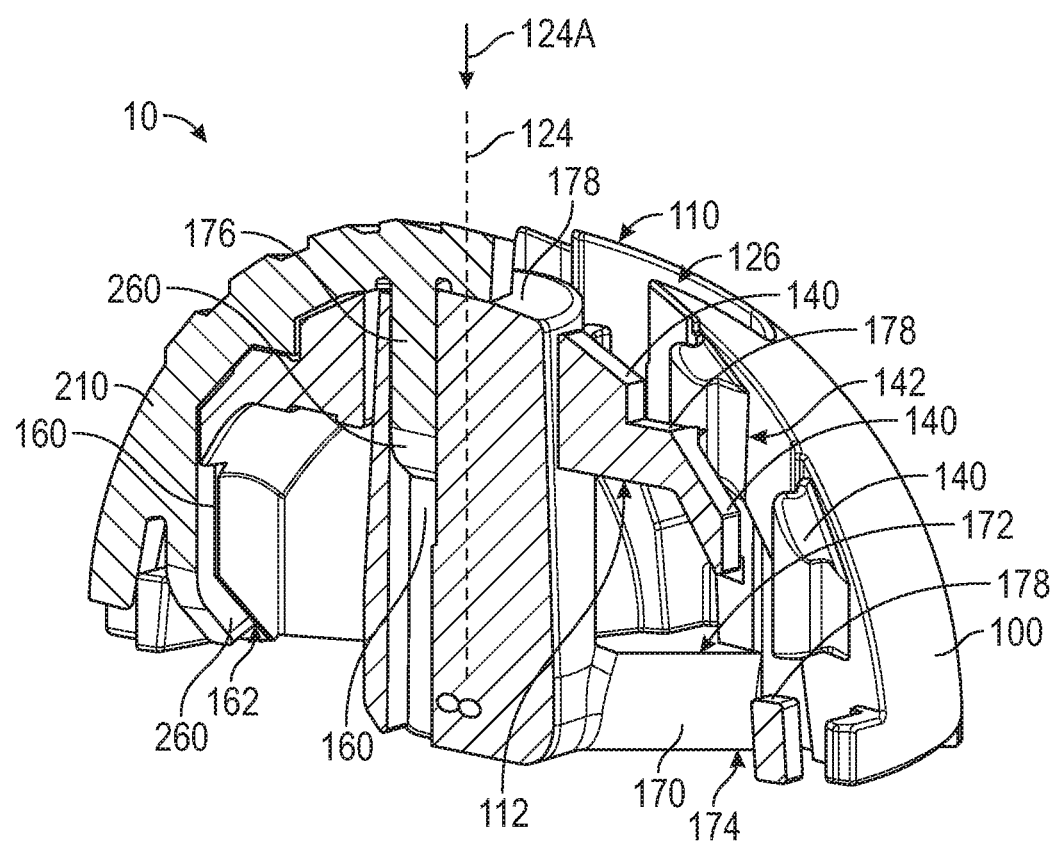
FIG. 3 shows a cross-sectional view of the body and one arcuate element of FIG. 1A taken along line A-A', in accordance with at least one example.
Figure 6:
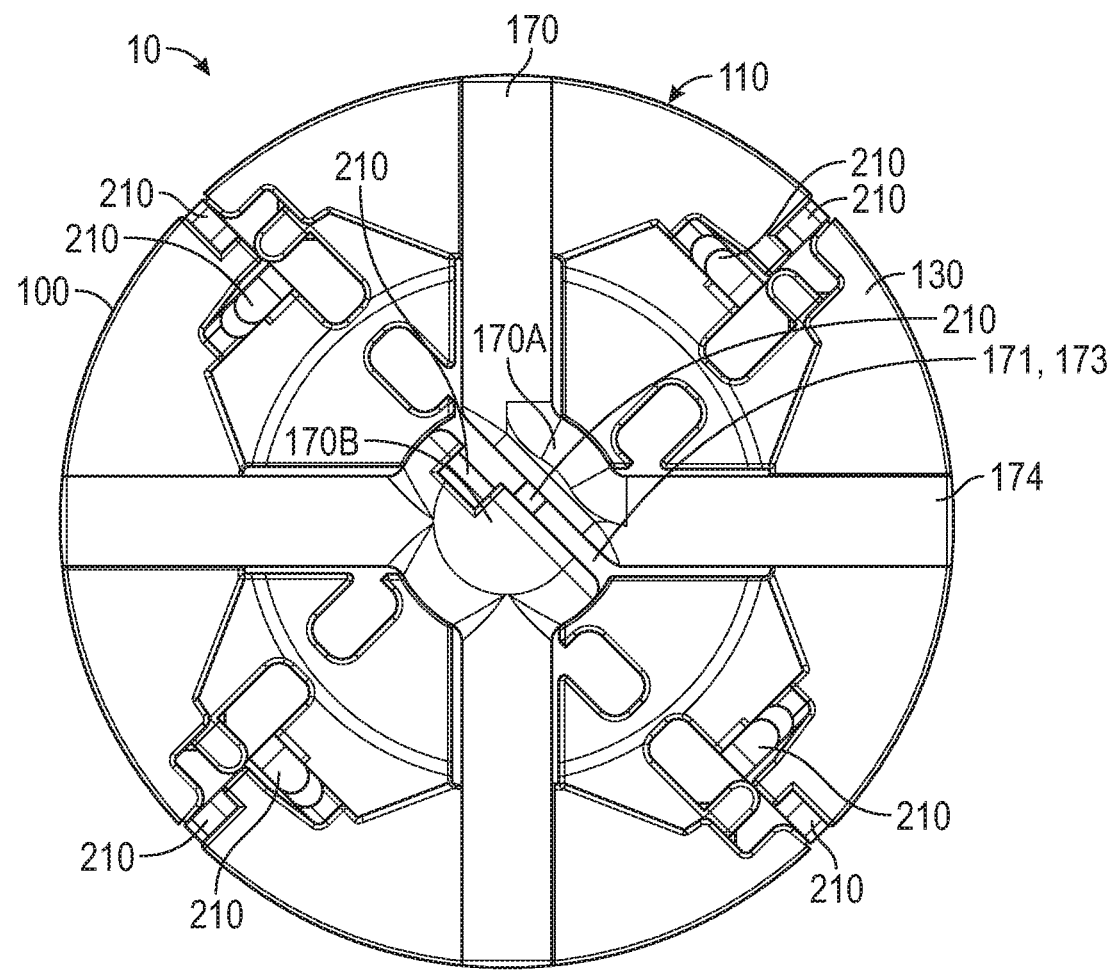
FIG. 6 shows a bottom view of the reamer head of FIG. 1A including the body and the cutting system, in accordance with at least one example.
Figure 7:
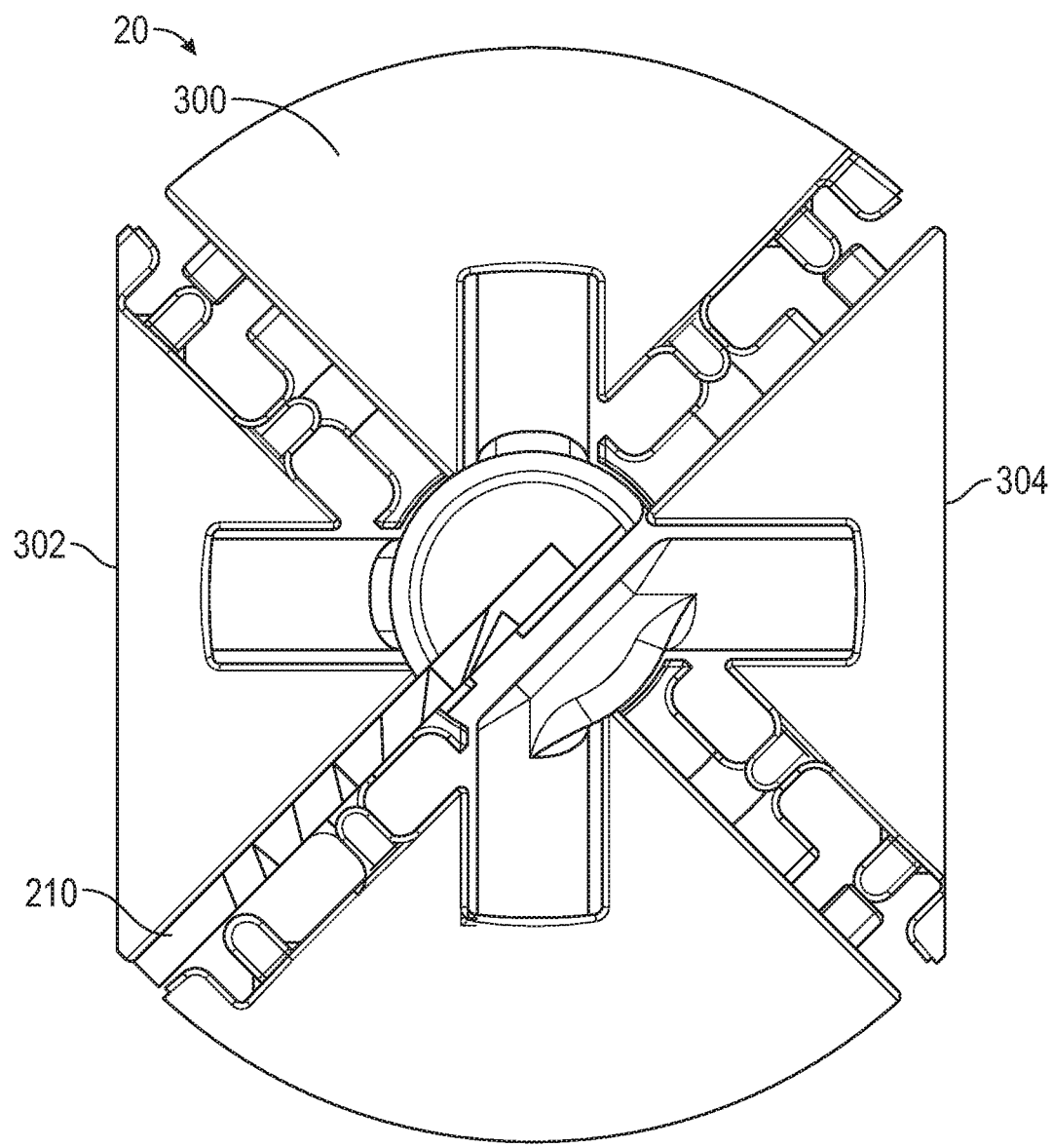
FIG. 7 shows a top view of another illustrative reamer head for minimally invasive surgery (MIS) including a body and at least one arcuate element, in accordance with at least one example.

In some examples, the body 100 can be formed of a plurality of polymeric materials and can include a single or multiple components integrally molded to one another. For example, a lower grade polymer can form the majority of the body 100, while a higher-grade polymer can be used to form the driver interface 170 (FIGS. 3, 6 and 7). The use of various polymeric materials can provide the necessary strength at the driver interface 170, while minimizing the cost of the rest of the body 100 by using a lower grade and less expensive polymeric material where feasible.

Referring to FIG. 1A, in a perspective view of the body 100, the body 100 can have an outer surface 110 (e.g., outer dome surface) that extends from an apex region 122 (e.g., proximate an apex 120) to a base 130. A recess 140 can be formed in the outer surface 110 to receive the cutting system 200. The recess 140 can include at least one arcuate channel 142 extending from a portion of the body 100 at or near the apex 120 towards the base 130. At or near the apex 120 can be defined as in the apex region 122, which is shown in further detail in FIG. 5.

Figure 5:
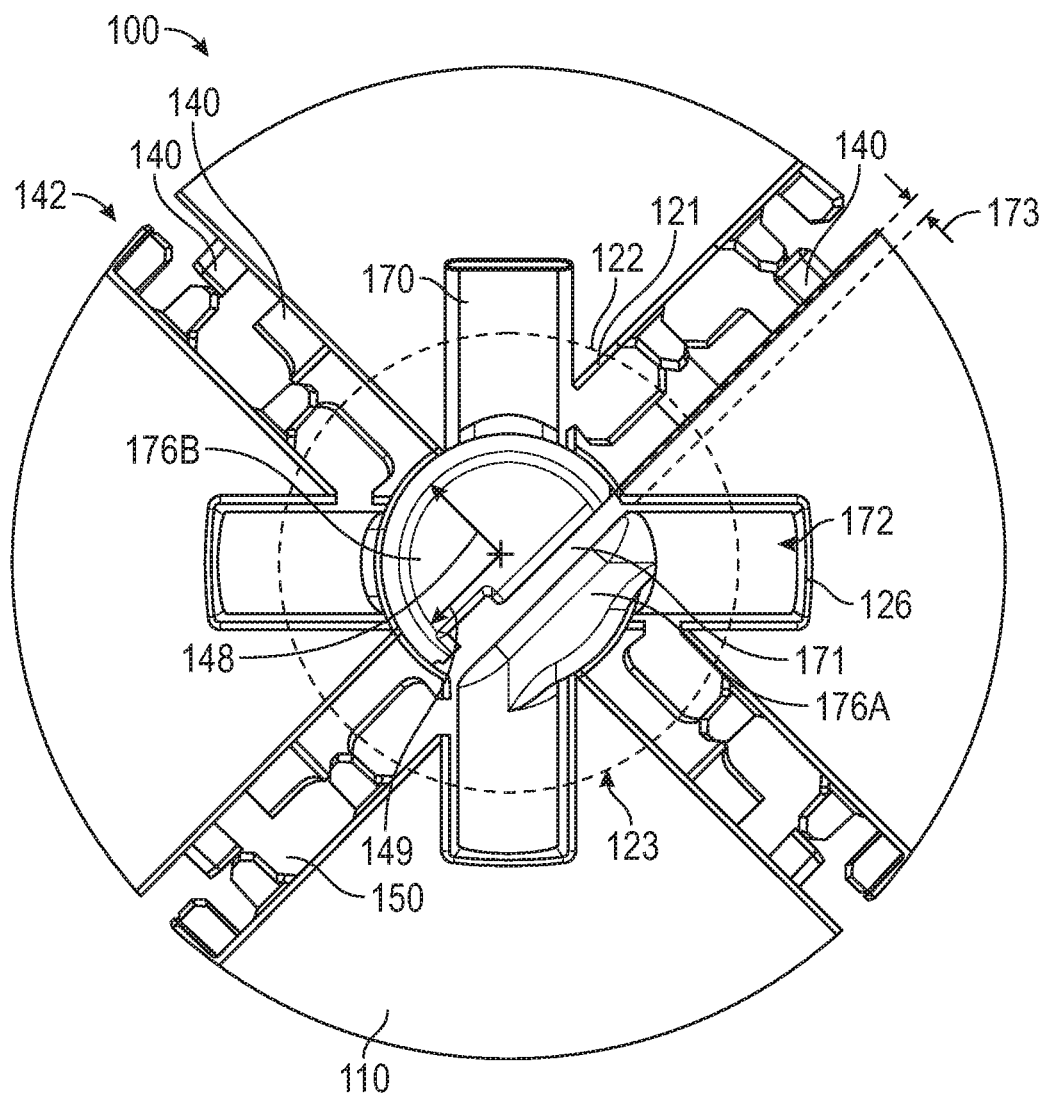
FIG. 5 shows a top view of the body of the reamer head of FIG. 1A without the cutting system, in accordance with at least one example.

As shown in the example of FIG. 1A, the recess 140 can include a plurality of arcuate channels 142 extending away from the apex 120 along a plurality of directions (e.g., 148, 149; FIG. 5). The plurality of directions 148, 149 can be described as beginning proximate the apex 120 (or apex region 122) and extending outward towards different locations along the base 130. As shown in FIG. 5, the plurality of arcuate channels 142 can be arranged in a generally starburst arrangement extending from the apex region 122.

In some examples, the recess 140 in the outer surface 110 that is configured to accept the cutting system 200 can be formed by multiple recess formations in the outer surface 110 and is not necessarily limited to a single recess, a continuous recess, or a recess of uniform depth. In some examples, the arcuate channels 142 that make up the recess 140 can include apertures (FIG. 5) having at least a portion that extends through a thickness of the body 100, the thickness extending from the outer surface 110 to an inner surface 112 (FIG. 3).

The illustrative body 100 of FIG. 1A shows the plurality of arcuate channels 142 as four arcuate channels 142 arranged in a generally starburst arrangement. However, in some examples, the recess 140 can include any number of arcuate channels 142, such as one, two, three, four, five, six, seven or eight arcuate channels 142, or more than eight arcuate channels 142. The starburst arrangement shown is merely one example of a starburst.

The body 100, having a generally dome or hemispherical shape, may not include a perfectly geometric apex 120, but rather an imaginary apex or apex region 122 proximate the location where the geometric apex would be located if the body 100 was an exact dome or hemisphere. In some examples, and as shown in FIG. 5, the apex region 122 can include a circumference around the apex 120 (imaginary apex or an apex axis 124) that extends outward to include a specified circumference 121. In some examples, the specified circumference 121 of the apex region 122 corresponds to the diameter 123 of the apex region 122. In some examples, the diameter 123 of the apex region 122 can be 1.5 inches around the apex axis 124 and extending from the outer surface 110 to the inner surface 112 along the apex axis 124 (FIG. 3). In a possibly more preferred example, the specified circumference 121 of the apex region 122 can include a smaller diameter 123 of 1.0 inches around the apex axis 124. In a possibly most preferred example, the specified circumference 121 of the apex region 122 can include a diameter 123 of 0.5 inches around the apex axis 124.

Figure 4:
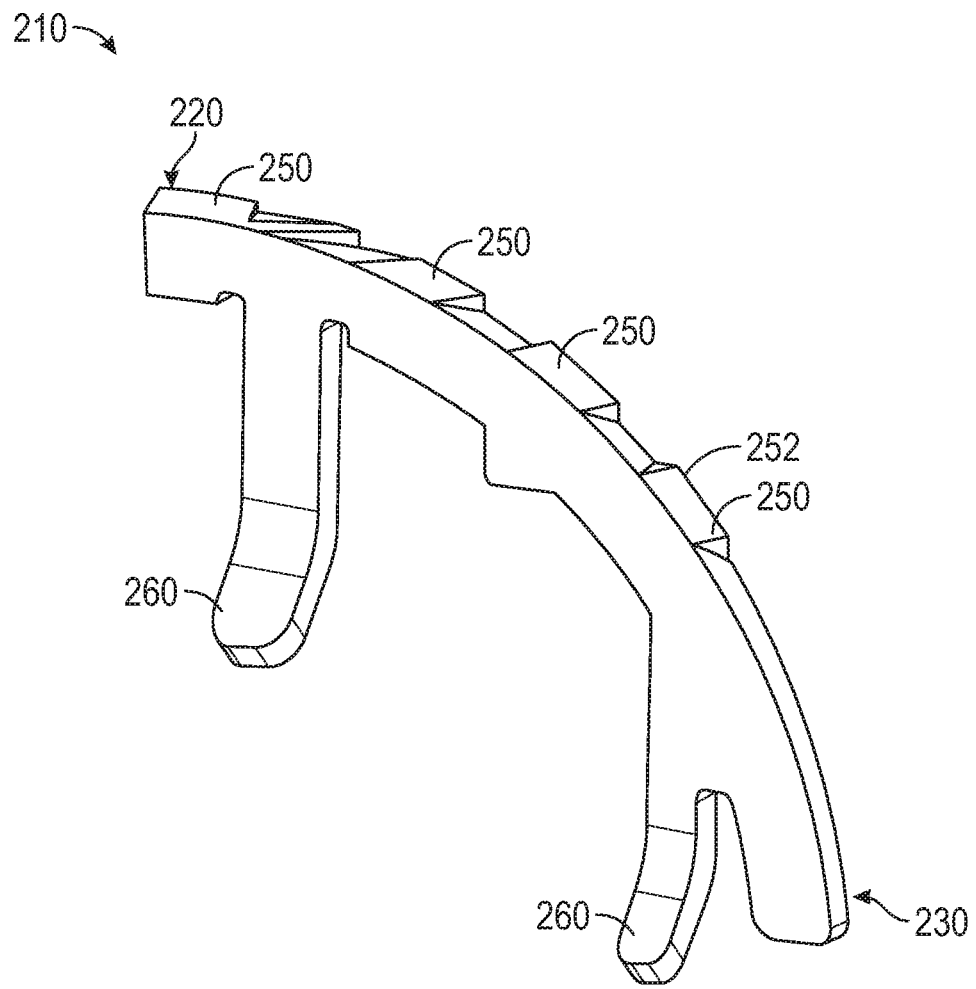
FIG. 4 shows the arcuate element of FIG. 1A, in accordance with at least one example.

The body 100 supports the cutting system 200 that facilitates the cutting action of the reamer head 10. As shown in the example of FIG. 1A, the cutting system 200 can include a plurality of arcuate elements 210 configured to cut bone. FIG. 4 shows a perspective view of an example arcuate element 210 of the cutting system without the body 100. As shown in FIG. 1A and FIG. 4 together, each of the arcuate elements 210 can extend from a first end portion 220 proximate the apex 120 to a second end portion 230 more distal from the apex 120, towards or proximate the base 130.

As shown in FIG. 1A, like the arcuate channels 142 of the body 100, the arcuate elements 210 of the cutting system 200 can also extend outward in a generally starburst arrangement. The generally starburst arrangement can include arcuate elements 210 extending away from the apex 120 (the imaginary apex, apex axis 124), or anywhere in the apex region 122 of the body 100 towards the base 130.

Also, like the arrangement of the arcuate channels 142, the cutting system 200 can include any number of arcuate elements 210, such as one, two, three, four, five, six, seven or eight arcuate elements 210, or more than eight arcuate elements 210. However, in at least one example, the reamer head 10 can include a single arcuate element 210 and a single arcuate channel 142.

Figure 1B:
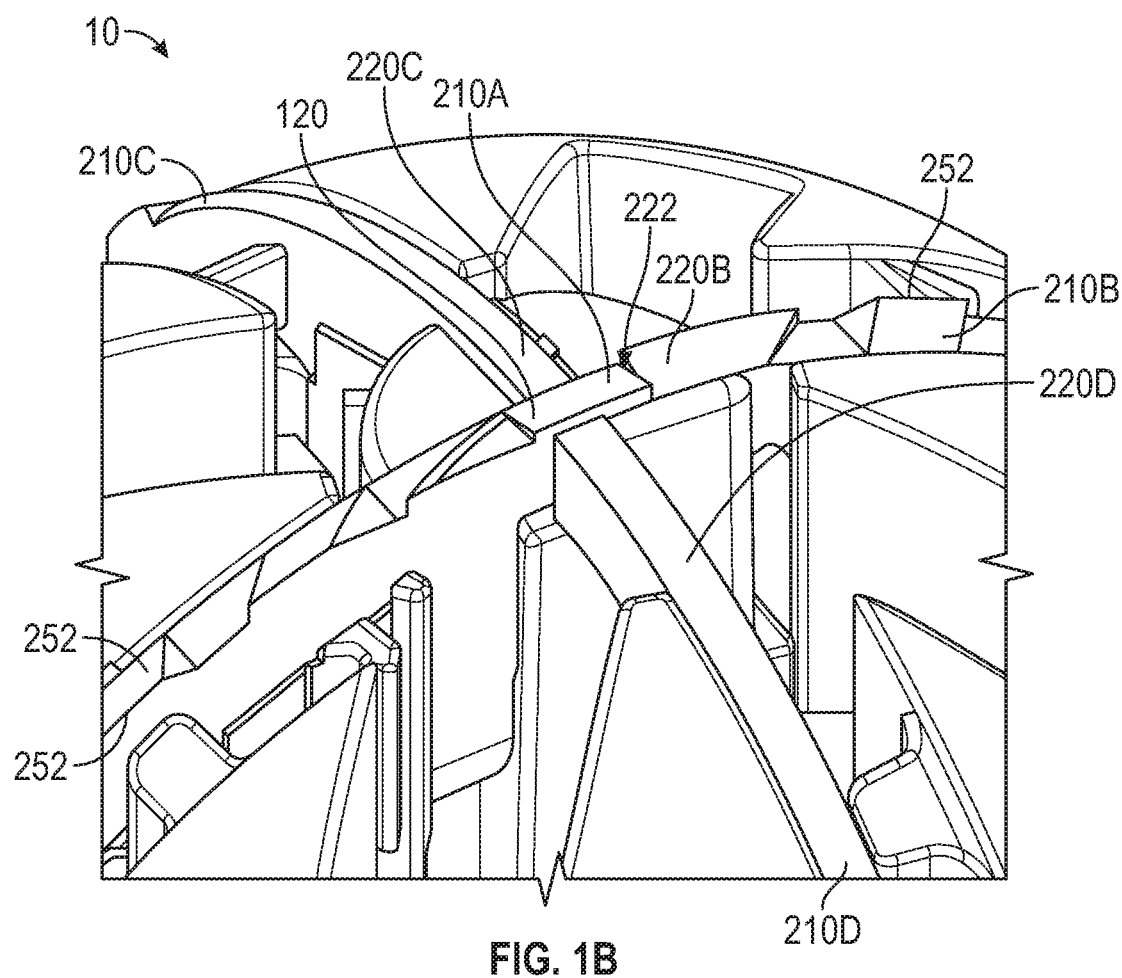
FIG. 1B shows a close-up perspective view of a portion of the reamer head of FIG. 1A, in accordance with at least one example.
Figure 2:
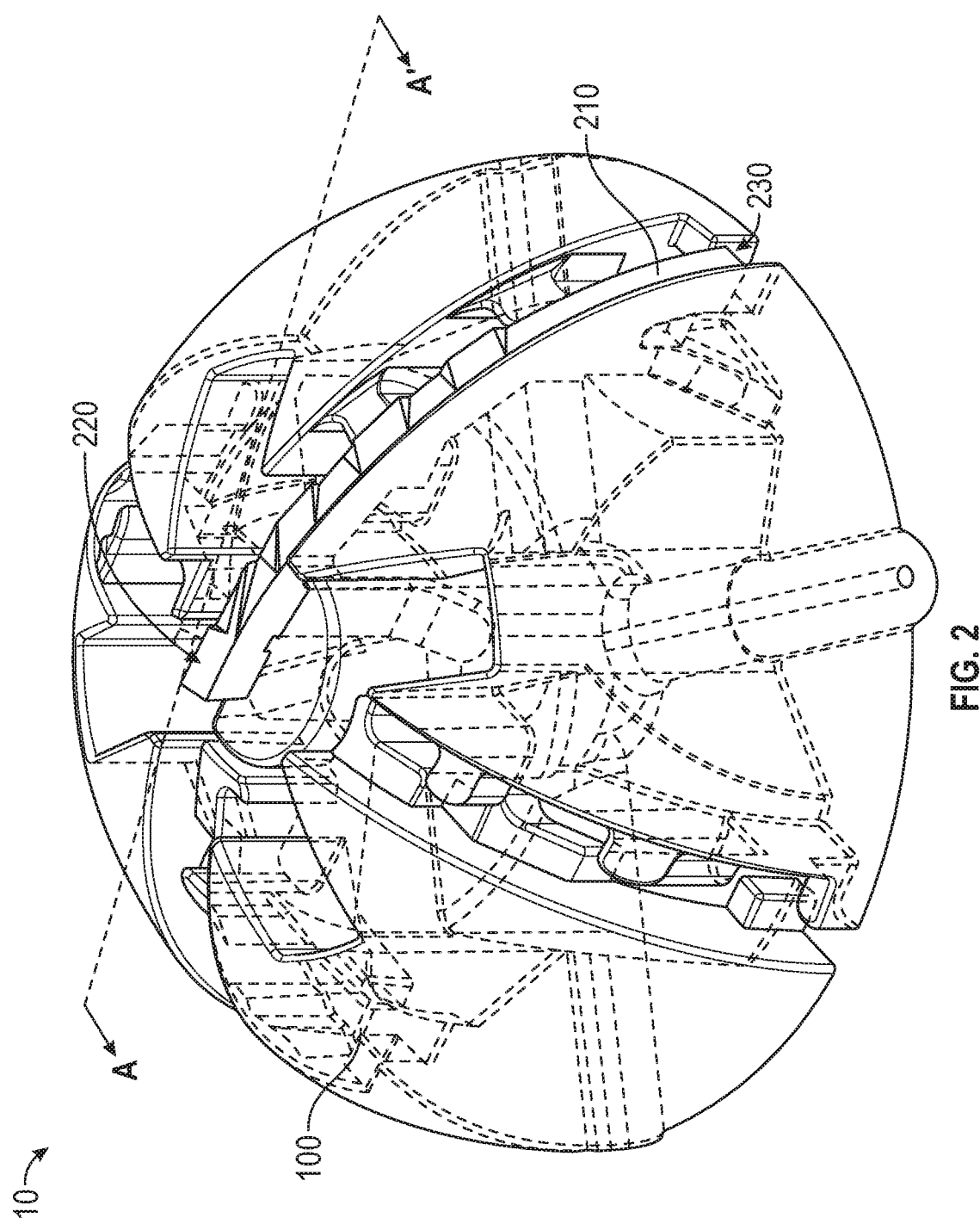
FIG. 2 shows another perspective the reamer head of FIG. 1A with the body shown as partially transparent and only one arcuate element shown in solid, in accordance with at least one example.

In some examples and as shown in the close-up view of FIG. 1B, first end portions 220 of at least two of the plurality of arcuate elements 210 can overlap or be located adjacent to one another. For example, as shown in FIG. 1B, at least one of the plurality of arcuate elements 210 can extend across the apex 120. For example, first end portion 220A of the arcuate element 210A can overlay the apex 120 (e.g., imaginary apex, or apex region 122). Other of the plurality of arcuate elements 210B, 210C, 210D can be located such that first end portions 220A, 220B, 220C of the arcuate elements 210B, 210C and 210D are located proximate the first end portion 220A of arcuate element 210A.

In at least one example, at least two of the first end portions 220A, 220B, 220C and 220D can be offset from one another, not in contact with each other, or spaced apart from one another away from the apex 120 but within the apex region 122.

As show in FIG. 1A, each of the plurality of arcuate elements 210 can be located in a respective one of the plurality of arcuate channels 142 formed in the body 100. The arcuate elements 210 can be coupled to the body 100, for example: by retention features that create a snap-fit connection between the arcuate elements 210 and the body 100; by integrally molding the arcuate elements 210 into the body 100; or by other attachment methods such as fasteners, adhesives or heat-staking. The cutting system 200 can be formed from stamped metal, such as surgical steel or another biocompatible material having sufficient strength to be retained by the body 100 and to cut bone.

As shown in FIGS. 1A, 3 and 4, at least one of the arcuate elements 210 can include the cutting elements 250 configured to remove bone. The cutting elements 250 can extend outward from the respective arcuate channel 142 beyond the outer surface 110. For example, the cutting elements 250 can extend outward radially from the generally hemispheric shaped body 100. Because the cutting elements 250 extend beyond the outer surface 110, when the reamer head 10 is placed at an implant site of the bone, such as an acetabulum, the cutting elements 250 can come into contact with the bone.

As shown in FIGS. 1A, 1B and 4, each arcuate element 210 can include a plurality of cutting elements 250. However, in some examples, one or more of the arcuate elements 210 can include a single cutting element 250, or different arcuate elements 210 can include different numbers, size, shape or arrangement of the cutting elements 250.

Although the number of arcuate elements in FIG. 1A is shown as four. In some examples, the arcuate elements 210 can be provided in multiples of four, such as four, eight or twelve arcuate elements 210. Having a plurality arcuate elements 210 in multiples of four can make it possible to tool and fabricate a reamer head more easily, while still being able to interface with conventional drivers that are designed to engage with a standard driver interface (e.g., 170; FIG. 6) having a four cross-bar arrangement. The depth of cut, the number of cutting elements 250 and orientation can be varied within the multiple of four to minimize tooling and fabrication costs. In other examples, different number of cutting elements and orientation can be provided, including a number that is not a multiple of four.

Another feature of the driver interface 170 can include an arcuate element support 176 as shown in FIGS. 1A and 3. The arcuate element support 176 can extend away from the driver interface 170 towards the apex region aperture 126 and can include a support surface(s) 178 configured to support one or more arcuate elements 210. The arcuate element support 176 can include a vertical channel 171 that extends parallel to the apex axis 124 (FIG. 3). In some examples the vertical channel 171 can be defined as a gap 173 between a first portion 176A of an arcuate element support 176 and a second portion 176B of an arcuate element support 176. In some examples the vertical channel 171 can be defined as a gap 173 between a first portion 170A of a driver interface 170 and a second portion 170B of a driver interface 170 (FIG. 6). In some examples the gap may be in a range between 0.1 inches and 0.4 inches.

To facilitate molding of the complex features of the body 100, including integrally molding the driver interface 170, the body 100 can include an apex region aperture 126 (FIGS. 1A, 3 and 5) extending from the outer surface 110 to the inner surface 172 of the body 100. The apex region aperture 126 can allow tooling for molding the arcuate element support 176 and/or driver interface 170 a passageway through the body 100 along the apex axis 124 (see, mold direction 124A in FIG. 3).

Integrally molding the driver interface 170 can include providing a first mold cavity that forms the apex region aperture 126 and/or the inner surface 172 of the driver interface 17. A second corresponding mold cavity can be supplied from the opposite side of the body 100 to mold the base 130 and/or an outer surface 174 of the driver interface 170 (FIGS. 3 and 6). In some examples, the apex region aperture 126 can be cross-shaped (e.g., generally cross-shaped) corresponding to the shape of the driver interface 170 to allow egress of the first mold cavity through the apex region aperture 126 following the molding process.

In some examples, the arcuate elements 210 can be formed into an arcuate shape prior to assembly with the body 100 as shown in FIG. 4. However, in some examples, the arcuate element 210 can be planar prior to assembly, and forced into a curved shape by attachment to the body 100, thus taking on the arcuate shape in the assembly process.

The arcuate elements 210 can be formed from stamped metal, such as surgical steel or can be formed of another biocompatible material.

In some examples, to provide a specific cutting sharpness, the cutting elements 250 can be sharpened after being stamped. In other examples, the cutting elements 250 may not be sharpened (e.g., no post processing) after being stamped. To achieve a specified sharpness without post-processing, the cutting elements 250 can be stamped such that a material blank for the arcuate element 210 is pierced at an angle (e.g., cutting elements 250 die cut to the shape shown in FIGS. 1B and 4) to create a breakaway edge 252 that results in a specified sharpness.

In some examples, cutting elements 250 can take on a variety of other forms including, protruding elements, studs, and abrasive materials. In some examples, the cutting elements can have three-dimensionally formed holes like a cheese grater.

With reference to FIG. 5, each of the plurality of arcuate channels 142 can extend in a different direction. For example, one of the arcuate channels 142 can extend generally along (but not necessarily aligned to) a first direction 148 from the apex 120 toward the base 130. Likewise, a second arcuate channel (another of 142) can extend generally along (but not necessarily aligned to) a second direction 149 from the apex 120 towards another location on the base 130. The second direction being different than the first direction.

In some examples, instead of providing individual arcuate elements 210 that extend along the same arc, two or more of the arcuate elements 210 can be incorporated into one longer arcuate element. For example, a single arcuate element that incorporates two of the arcuate elements 210 into one longer arcuate element can extend from proximate one portion of the base 130, over the apex region 122 and down towards the opposite side of the base 130.

As shown in the cross-sectional view of FIG. 3, a snap-fit connection can be used to secure the arcuate elements 210 to the body 100. For example, the retention elements 260 can be slid into retention apertures 160 in the body 100. The body 100 can further include retention surfaces 162 configured to receive the retention elements 260. The retention surfaces 162 can retain the arcuate elements 210 in the arcuate channels 142.

As shown in FIG. 3, the retention surfaces 162 can capture the retention element 260 of the arcuate element 210 to prevent the arcuate element 210 from being removed from the arcuate channel 142. The retention surfaces 162 and retention elements 260 can be any curved, planar or irregularly shaped features that are suitable for providing a secure snap-fit connection.

With reference to FIG. 5, the body 100 can include one or more bone disposal apertures 150 extending through the body 100 from the outer surface 110 to an inner surface 112 that is opposite the outer surface 110 (FIG. 3). The one or more bone disposal apertures 150 can allow bone that has been cut from the bone site to be collected and removed from the bone site. Removing the bone prevents bone or other tissue fragments from interfering with the implant. In addition, the removed bone can be mixed with other materials to fill voids between the bone surface and the implant. In some examples, each of the arcuate channels 142 can include a respective bone disposal aperture 150.

FIG. 7 shows a top view of another illustrative orthopedic reamer head 20. Reamer head 20 shares similarities with the example of reamer head 10 of FIGS. 1A, 1B and 2-6, therefore it is understood that features described with respect to the example of FIGS. 1A, 1B and 2-6 can be included in reamer head 20 and vice-versa. In addition, like numerals can represent like elements, and therefore all the features of reamer head 20 will not be described in full detail.

Reamer head 20 shows an example of an orthopedic tool having a reduced size over a standard tool. Reamer head 20 is designed to provide the benefits of reamer head 10 but also be capable of fitting into a smaller incision during minimally invasive surgery (MIS). In some examples, the reamer head 20 is similar to the reamer head 10 except that the dome or hemispherical-shape of the body 100 is a truncated dome or hemisphere to be able to fit into the smaller MIS incision. For example, the body 300 includes opposing first and second truncated portions 302, 304.

Reamer head 20 can otherwise include a body 300 that is generally dome shaped and similar to body 100 (except for the truncated portions 302, 304) and can include the cutting system 200 coupled to the body 300. The body 300 can have the various recesses and apertures extending therethrough as previously described in the examples of FIGS. 1A, 1B and 2-6.

Figure 8:
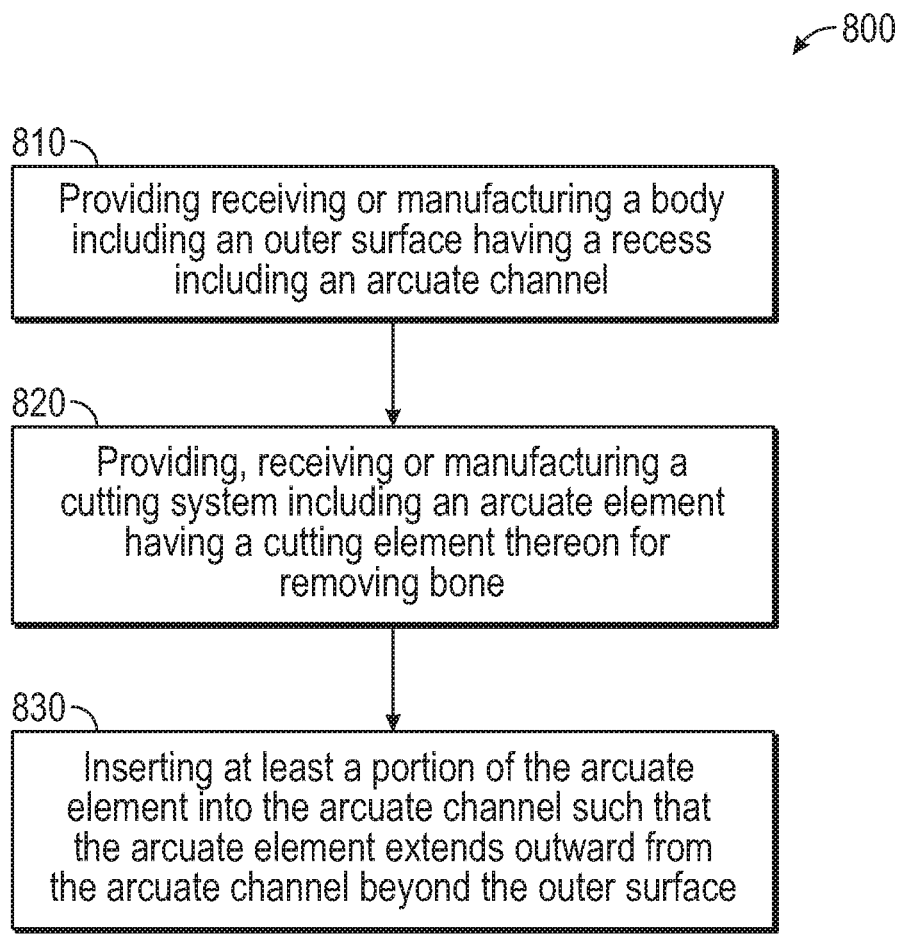
FIG. 8 is a flow chart illustrating an example method of manufacturing the orthopedic reamer heads described herein, in accordance with at least one example.

FIG. 8 shows a flow chart illustrating an example method of manufacturing 800 the reamer head 10 of FIGS. 1A, 1B and 2-6. The example method of manufacturing 800 (hereinafter method 800) described herein is merely illustrative in nature. Although aspects of the method 800 can be used with and will be described with reference to the example reamer head 10, the method 800 can also be used with other reamer heads (including reamer head 20 of FIG. 7) or other orthopedic tools. The method 800 is not limited to the steps specified herein. The method 800 can include fewer steps or additional method steps other than those described in this disclosure.

Step 810 can include providing, receiving or manufacturing a body 100. The body 100 can have a generally dome shape including an outer surface 110 extending from an apex region 120 to a base 130. The outer surface 110 can include a recess 140 extending along a direction from the apex region 122 (e.g., proximate the apex or an imaginary apex 120) towards the base 130. The recess 140 can include at least one arcuate channel 142. In some examples, the recess 140 is a plurality of recesses that together form the at least one arcuate channel 142.

In some examples, step 810 can include integrally molding a driver interface with the body. Integrally molding a driver interface 170 with the body 100 can include providing, receiving or manufacturing a first mold cavity that forms an apex region aperture 126 proximate the apex 120 or apex region 122 of the body 100.

Step 820 can include providing, receiving or manufacturing a cutting system 200 including an arcuate element 210 extending from a first end portion to a second end portion, the arcuate element 210 including a cutting element for removing the bone. In some examples the cutting system 200 can include a one-piece design.

Step 830 can include inserting at least a portion of the arcuate element 210 into an arcuate channel 142 such that at least a portion of the arcuate element 210 extends outward from the arcuate channel 142 beyond the outer surface 110 of the body 100.

Step 830 can further include engaging a retention element 260 of the arcuate element 210 with a retention surface 162 on the body 100 such that the arcuate element 210 is retained by the body 100 with at least a portion of the cutting element 250 remaining extended outward beyond the outer surface 110.

In some examples the inserting step 830 can include inserting a plurality of the arcuate element 210 into a plurality of the arcuate channel 142. In some examples, inserting the plurality of arcuate elements 210 into the plurality of arcuate channels 142 can include repeating step 830 until the plurality of arcuate elements 210 are arranged in a starburst formation along the outer surface 110. The starburst formation extending away from the apex 120 (or the imaginary apex), or the apex region 122 of the body 100 towards the base 130.

As the arcuate elements 210 are inserted into the arcuate channels 142, step 830 can include placing first end portions 220A, 220B, 220C, 220D of the arcuate elements 210A, 210B, 210C, 210D adjacent to one another as shown in FIG. 1B. In some examples, at least one of the plurality of arcuate elements 210 can extend across the apex 120. For example, each of the plurality of arcuate elements 210 can be inserted into one of the plurality of arcuate channels 142, and when at least one of the arcuate elements (e.g., 210A; FIG. 1B) is fully seated in the arcuate channel 142, the first end portion 220A of the arcuate element 210A can overlay the apex 120 (e.g., proximate, near, on, over the apex 120, imaginary apex, or apex region 122). As a second or subsequent arcuate elements (e.g., 210B, 210C, 210D; FIG. 1B) are inserted and seated, the first end portions 220 of the arcuate elements 210B, 210C and 210D can be placed proximate the first end portion 220A of arcuate element 210A. In some examples, step 830 can include overlapping at least two of the plurality of arcuate elements 210 proximate an apex region 122.

The method 800 provides reamer heads, including but not limited to reamer head 10, having a modular design that can be made cost effective enough for disposable applications, without sacrificing the performance provided in a re-usable reamer head design.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

Numbered Examples

Example 1 is an orthopedic reamer head for preparing a bone to receive an implant, the orthopedic reamer head comprising: a body having a generally dome shape and an outer surface extending from an apex region to a base, the outer surface having a recess including an arcuate channel; and a cutting system having an arcuate element, the arcuate element including a cutting element for removing bone, wherein at least a portion of the arcuate element is located in the arcuate channel and at least a portion of the cutting element extends out of the arcuate channel beyond the outer surface.

In Example 2, the subject matter of Example 1 includes, wherein the arcuate channel extends along a direction from proximate the apex region towards the base.

In Example 3, the subject matter of Examples 1-2 includes, wherein the arcuate element extends from a first end portion proximate the apex region to a second end portion proximate the base.

In Example 4, the subject matter of Example 3 includes, wherein the arcuate element extends across an apex of the body.

In Example 5, the subject matter of Examples 3-4 includes, wherein the recess includes a plurality of the arcuate channel, and wherein the cutting system comprises a plurality of the arcuate element, and wherein each of the plurality of arcuate elements are located in one of the plurality of arcuate channels.

In Example 6, the subject matter of Example 5 includes, wherein each of the plurality of arcuate elements extend away from the apex region such that the cutting system is arranged in a starburst formation.

In Example 7, the subject matter of Examples 1-6 includes, wherein the body has a thickness extending from the outer surface to an inner surface opposite the outer surface, and wherein the apex region comprises an apex region aperture extending from the outer surface to the inner surface.

In Example 8, the subject matter of Examples 1-7 includes, a bone disposal aperture extending through the body from the outer surface to an inner surface opposite the outer surface.

In Example 9, the subject matter of Examples 1-8 includes, wherein the body is generally hemispherical-shaped.

Example 10 is an orthopedic reamer head for preparing a bone to receive an implant, the orthopedic reamer head comprising: a body including a generally hemispherical-shaped dome having an outer dome surface extending from an apex region to a base, the outer dome surface having a recess including a plurality of arcuate channels, the plurality of arcuate channels extending from the apex region towards the base, the plurality of arcuate channels arranged in a starburst arrangement; and a cutting system having a plurality of arcuate elements extending outward in a starburst arrangement from the apex region to second end portions towards the base, wherein each of the plurality of arcuate elements is located in one of the plurality of arcuate channels, wherein at least one of the plurality of arcuate elements includes, a cutting element for removing the bone and wherein the cutting element extends outward from the one of the plurality of arcuate channels beyond the outer dome surface.

In Example 11, the subject matter of Example 10 includes, a driver interface extending across the base of the body, the driver interface including an arcuate element support extending away from the driver interface towards the apex region, wherein the arcuate element support includes a support surface configured to support at least one of the plurality of arcuate elements.

In Example 12, the subject matter of Examples 10-11 includes, wherein the body has a thickness extending from an inner surface to an outer dome surface, and wherein the apex region comprises an apex region aperture extending from the outer dome surface to the inner surface.

In Example 13, the subject matter of Example 12 includes, wherein the apex region aperture is generally cross-shaped.

In Example 14, the subject matter of Examples 10-13 includes, wherein at least one of the plurality of arcuate elements extends across an apex of the body.

In Example 15, the subject matter of Examples 10-14 includes, wherein the apex region includes an apex axis and extends outward along an apex axis to include a circumference around the apex axis having a diameter of 1.5 inches.

Example 16 is a method of manufacturing an orthopedic reamer head for preparing a bone, the method comprising: providing, receiving or manufacturing a body having a generally dome shape including an outer dome surface extending from an apex region to a base, the outer dome surface having a recess extending along a direction from the apex region to the base, the recess including an arcuate channel; providing, receiving or manufacturing a cutting system including an arcuate element, the arcuate element including a cutting element for removing the bone; and inserting at least a portion of the arcuate element into the arcuate channel, wherein at least a portion of the arcuate element extends outward from the arcuate channel beyond the outer dome surface.

In Example 17, the subject matter of Example 16 includes, engaging the arcuate element with a retention surface on the body such that the arcuate element is retained by the body with at least a portion of the cutting element remaining extended outward beyond the outer dome surface.

In Example 18, the subject matter of Examples 16-17 includes, wherein the inserting the at least a portion of the arcuate element into the arcuate channel includes inserting a plurality of arcuate elements into a plurality of arcuate channels, wherein the plurality of arcuate channels are arranged in a generally starburst formation along the outer dome surface extending away from the apex region of the body towards the base.

In Example 19, the subject matter of Examples 16-18 includes, wherein at least one of the plurality of arcuate elements extends across an apex of the body.

In Example 20, the subject matter of Examples 18-19 includes, integrally molding a driver interface with the body, wherein integrally molding a driver interface includes providing, receiving or manufacturing a first mold cavity that forms an apex region aperture proximate the apex region of the body.

Example 21 is at least one machine-readable medium including instructions that, when executed by processing circuitry, cause the processing circuitry to perform operations to implement of any of Examples 1-20.

Example 22 is an apparatus comprising means to implement of any of Examples 1-20.

Example 23 is a system to implement of any of Examples 1-20.

Example 24 is a method to implement of any of Examples 1-20.

What is claimed is:

1. An orthopedic reamer head for preparing a bone to receive an implant, the orthopedic reamer head comprising:
   a body having a generally dome shape and an outer surface extending from an apex region to a base, the outer surface having a recess including a plurality of arcuate channels, each of the arcuate channels extending from the apex region toward the base; and
   a cutting system having a plurality of arcuate elements, each of the arcuate elements extending from a first terminal end adjacent to the apex region to a second terminal end adjacent to the base and including a cutting element for removing bone and a retention flange extending from a side of the arcuate element opposite of the cutting element, wherein at least a portion of each of the arcuate elements is located in a different one of the arcuate channels and at least a portion of each of the cutting elements extends out of the respective arcuate channel beyond the outer surface, and wherein each of the retention flanges is at least partially received within a retention aperture in the body and forms a snap-fit connection therewith.

2. The orthopedic reamer head of claim 1, wherein the arcuate elements extend across an apex of the body.

3. The orthopedic reamer head of claim 1, wherein each of the plurality of arcuate elements extends away from the apex region such that the cutting system is arranged in a starburst formation.

4. The orthopedic reamer head of claim 1, wherein the body has a thickness extending from the outer surface to an inner surface opposite the outer surface, and wherein the apex region comprises an apex region aperture extending from the outer surface to the inner surface.

5. The orthopedic reamer head of claim 1, further comprising a bone disposal aperture extending through the body from the outer surface to an inner surface opposite the outer surface.

6. The orthopedic reamer head of claim 1, wherein e body is generally hemispherical-shaped.

7. The orthopedic reamer head of claim 1, wherein the arcuate channel includes a bone disposal aperture located directly adjacent to the cutting element.

8. The orthopedic; reamer head of claim 1, wherein the arcuate element includes a plurality of retention flanges extending from the side of the arcuate element opposite of the cutting element that are at least partially received within a corresponding plurality of retention apertures in the body.

9. An orthopedic reamer head for preparing a bone to receive an implant, the orthopedic reamer head comprising:
   a body including a generally hemispherical-shaped dome having an outer dome surface extending from an apex region to a base, the outer dome surface having a recess including a plurality of arcuate channels, each of the plurality of arcuate channels extending from the apex region towards the base, the plurality of arcuate channels arranged in a starburst arrangement; and
   a cutting system having a plurality of arcuate elements extending outward in a starburst arrangement from the apex region to second end portions towards the base,
   wherein each of the plurality of arcuate elements is located in one of the plurality of arcuate channels,
   wherein each of the plurality of arcuate elements extends from a first terminal end at the apex region to a second terminal end at the base,
   wherein at least one of the plurality of arcuate elements includes a cutting element for removing the bone and a retention flange extending from a side of the arcuate element opposite of the cutting element,
   wherein the retention flange is at least partially received within a retention aperture in the body and forms a snap-fit connection therewith, and
   wherein the cutting element extends outward from the one of the plurality of arcuate channels beyond the outer dome surface.

10. The orthopedic reamer head of claim 9, further comprising a driver interface extending across the base of the body, the driver interface including an arcuate element support extending away from the driver interface towards the apex region, wherein the arcuate element support includes a support surface configured to support at least one of the plurality of arcuate elements.

11. The orthopedic reamer head of claim 9, wherein the body has a thickness extending from an inner surface to an outer dome surface, and wherein the apex region comprises an apex region aperture extending from the outer dome surface to the inner surface.

12. The orthopedic reamer head of claim 11, wherein the apex region aperture is generally cross-shaped.

13. The orthopedic reamer head of claim 9, wherein at least one of the plurality of arcuate elements extends across an apex of the body.

14. The orthopedic reamer head of claim 9, wherein the apex region includes an apex axis and extends outward along an apex axis to include a circumference around the apex axis having a diameter of 1.5 inches.

* * * * *